United States Patent [19]
Sawyer et al.

[11] Patent Number: 4,784,644
[45] Date of Patent: Nov. 15, 1988

[54] VALVE, CATHETER AND METHOD FOR PREVENTING THE INTRODUCTION OF AIR INTO THE BODY OF A PATIENT

[75] Inventors: Philip N. Sawyer, Brooklyn; Joseph F. Fitzgerald, Queens, both of N.Y.; Lester F. Miller, Danbury, Conn.

[73] Assignee: Interface Biomedical Laboratories Corp., Brooklyn, N.Y.

[21] Appl. No.: 50,589

[22] Filed: May 15, 1987

Related U.S. Application Data

[63] Continuation-in-part of Ser. No. 818,434, Jan. 13, 1986, Pat. No. 4,721,725, and a continuation-in-part of Ser. No. 484,205, Apr. 12, 1983, Pat. No. 4,684,364, and a continuation-in-part of Ser. No. 511,256, Jul. 6, 1983, Pat. No. 4,568,333.

[51] Int. Cl.$^4$ ............................................. A61M 25/00
[52] U.S. Cl. .................................. 604/122; 604/247; 137/843; 137/493
[58] Field of Search .................... 604/122, 247, 250; 137/846, 847, 849, 850, 493, 843, 852

[56] References Cited

U.S. PATENT DOCUMENTS

| | | | |
|---|---|---|---|
| 605,693 | 6/1898 | Black | 137/843 |
| 3,298,391 | 1/1967 | Savage | 137/493 |
| 3,324,877 | 6/1967 | Bochan | 137/846 X |
| 3,572,375 | 3/1971 | Rosenberg | 604/247 X |

Primary Examiner—Stephen C. Pellegrino
Attorney, Agent, or Firm—Pennie & Edmonds

[57] ABSTRACT

A method for preventing the introduction of air into the vascular system of a patient during intravenous or intra-arterial procedures, as well as for preventing the reflux of fluids into the body of a patient. Also, novel fluid directing means and catheters which include integral or attached fluid flow control means for use in this method.

25 Claims, 2 Drawing Sheets

FIG. 2
FIG. 3
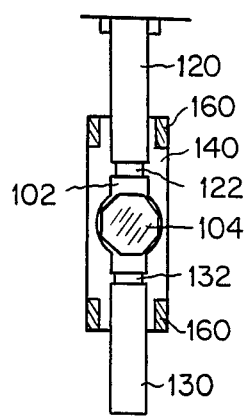
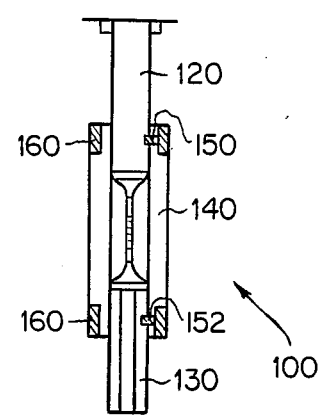
FIG. 4
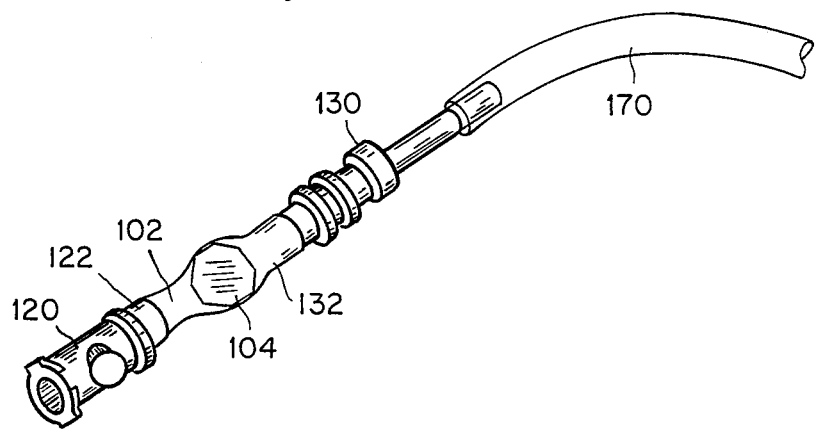

VALVE, CATHETER AND METHOD FOR PREVENTING THE INTRODUCTION OF AIR INTO THE BODY OF A PATIENT

CROSS-REFERENCE TO RELATED APPLICATION

This application is a continuation-in-part of application Ser. No. 818,434 filed Jan. 13, 1986, now U.S. Pat. No. 4,721,725 a continuation-in-part of application Ser. No. 484,205, filed Apr. 12, 1983, now U.S. Pat. No. 4,684,364 and a continuation-in-part of application Ser. No. 511,256, filed July 6, 1983, now U.S. Pat. No. 4,568,333.

TECHNICAL FIELD

This invention relates to a valve, catheter and method for preventing the entry of air into the vascular system of a patient during intravenous or intra-arterial procedures. The invention can also be used for preventing the reflux of fluids, such as urine, back into the body of the patient when such fluids are removed by catheter means.

BACKGROUND

Procedures have long been known involving the introduction or removal of fluids into or from the vascular system or body cavity of a patient. For the introduction of fluids, these have developed to a point of employing a source of fluid for intravenous procedures and connecting such source, often via a pump, through a needle or catheter into the vascular system. The pump itself has been developed to a point that when connecting catheters are accidentally opened to ambient atmosphere, the pumping operation is terminated thereby to reduce the possibilities of air being introduced into the vascular system. This is necessary because the introduction of air will cause an air embolism which in turn may be fatal to the patient being treated. Nevertheless, the use of such a pump, which is commercially available, is not effective to prevent accidents of the aforenoted type in all cases. Thus, for example, when the intravenous tubing is coupled to a catheter situated on the downstream side of the pump, and this catheter becomes accidentally opened to ambient atmosphere, the pressure differential between ambient atmosphere and the vascular system in which the distal tip of the catheter resides (particularly in the chest and/or abdomen) is such as to cause air to be sucked through the catheter into the vascular system. Also, when the fluid is introduced by gravity flow, this problem can result from an accidental opening or separation of the catheter or the fluid supply. This accidental occurrence has been known to cause serious harm or death to the patient being treated.

A number of U.S. patents have been found which attempt to resolve problems of the aforenoted type, as well as to related systems exposed to pressure differential or the like. These patents include U.S. Pat. Nos. 2,538,662; 3,570,808; 3,599,670; 3,888,249; 4,103,686; 4,252,166; 4,324,239; and 4,335,747.

Abbott in U.S. Pat. No. 2,538,662 discloses a surgical apparatus for the intravenous administration of liquids, such as whole blood, blood plasma, dextrose solutions, and the like and is directed particularly to an expendable valve unit construction used in such surgical apparatus.

Wren in U.S. Pat. No. 3,570,808 discloses a coupling assembly for releasably attaching an air hose to a regulator of the type used in conjunction with the face mask of an underwater diving apparatus. The coupling is readily detachable and a valve mechanism is provided so that when the air hose is decoupled from the regulator underwater, the valves provided in the regulator air inlet and in the end of the air hose are immediately biased to a closed position. Such a construction and arrangement may have utilization in connection with intravenous procedures.

Simon in U.S. Pat. No. 3,595,228, discloses a portable alarm device attached to a coupling in a therapeutic apparatus to provide an alarm to alert hospital personnel under certain dangerous conditions as might apply to a respirator flow line or a tracheostomy tube assembly for indicating a break therebetween.

In U.S. Pat. No. 3,599,670, Gurner discloses a fluid coupling with a valve means having such provision that if a maximum rate of flow through a hose is exceeded as, for example, by leakage, the coupling valve will close and prevent further flow.

In U.S. Pat. No. 3,888,249, Spencer discloses a catheter for prolonged infusion of medication into an artery. The catheter is provided with a tip design employing a flap valve principle to assure uniform and steady diffusion of the medication into the blood stream and to inhibit retrograde flow of blood into the catheter thereby to minimize clotting in the catheter and blockage of medication flow.

Harverland discloses in U.S. Pat. No. 3,906,034 a pressure sensor-timer alarm for pressure sensitive devices wherein a plunger, having a magnetically mounted swith actuator, actuates a switch in response to pressure changes from a diaphragm. A failure to actuate the switch in either phase of the breathing cycle within a preset time causes the actuation of an alarm.

Winicki discloses in U.S. Pat. No. 4,067,329 a warning device which is actuated by the disconnection of a tube from another tube such as, for example, of a respirator cannula from a patient's medical apparatus.

In U.S. Pat. No. 4,103,686, LeFevre discloses a dual valve assembly for intravenous infusions from multiple parenteral fluid sources. The assembly controls forward and reverse flow through a flow line and includes normally seated first and second valves mounted for movement toward and away from respective valve seats to control flow in such a manner as to prevent reverse flow through the assembly.

Gordon shows in U.S. Pat. No. 4,324,239 a safety valve for preventing air embolism and hemorrhage. The safety valve disclosed is useful for catheterization procedures and is characterized by a piston having an internal flow path and so arranged as to be biased to a closed position. The arrangement is such as to prevent air embolism and hemmorhage.

In U.S. Pat. No. 4,335,747, Mitsumoto et al. disclose an arrangement which is effective to exclude air or other undesirable gas in a connecting procedure.

None of the aforegoing patents, nor any of the other arrangements known heretofore, however, is as effective as the present invention for preventing the introduction of air into the vascular system of a patient, or for preventing the reflux of fluids back into the organ or portion of the body from which such fluids were removed.

SUMMARY OF THE INVENTION

The invention relates to a fluid flow control means comprising tubular means having open input and output bores connected by channel means and operable between an open position to allow fluid flow therethrough and a closed position to prevent ambient pressure air from passing therethrough; and obturating means located within the channel means for prestressing and maintaining a portion of the channel means in a closed position. The channel means is forceable to open position in response to a positive fluid pressure in the input or output bore of the tubular means to allow fluid flow through the channel means from the bore containing the positive pressure to the other bore. The fluid flow control means is capable of passing fluid in either direction depending upon which bore contains the positive pressure, while the obturating means returns the channel means to a closed position when the positive pressure is removed.

In this fluid flow control means, the obturating means is preferably disc means for maintaining the tubular means in a substantially flat configuration, and the tubular means is a silicon tube. If desired, concentric housing means for enclosing the tubular means and obturating means may be used.

The invention also relates to catheter means comprising an elongated body portion for insertion into a patient; an integral hub portion adjacent to the body portion for introducing or removing fluids through the body portion; and the fluid flow control means described above.

In the catheter means, the fluid flow control means may be integral with the body portion or the hub portion. Also, means to maintain the fluid flow control means in an open position to facilitate the introduction of second catheter means, trocar means, needle means or fluid directing means, can be used if desired.

Alternately, the fluid flow control means may be releasably secured to the hub portion. For specific applications, two integral hub portions may be provided where each hub includes fluid flow control means located adjacent thereto. Thus, a first hub portion could allow the introduction of a fluid into a portion of the body of the catheter means and a second hub portion could allow a fluid to be removed from another portion of the body of the catheter means. The first hub portion may also include fluid flow control means which remains competent in response to fluid reflux or ambient air pressure but which opens in response to a positive fluid pressure above that of ambient air, while the second hub portion includes fluid flow control means which remains competent in response to fluid reflux but which opens in response to fluid pressure in the catheter body.

In either embodiment, the end of the body portion of the catheter opposite the hub portion may include a plurality of apertures to facilitate fluid collection or removal.

Another embodiment of the invention relates to a method for preventing the introduction of air into the vascular system of a patient through catheter means during intravenous or intra-arterial procedures which comprises providing catheter means with the fluid flow control means described above; introducing the catheter means into the vascular system of the patient during intravenous or intra-arterial procedures; and introducing a fluid into the patient through the fluid flow control means and catheter means by directing the fluid under a positive pressure into the bore of the input means of the fluid flow control means so that the fluid flow control means opens in response to said positive fluid pressure to allow flow therethrough, but remains competent in response to ambient air pressure in the bore of the input means to prevent the introduction of air into the vascular system of the patient.

Another method of the invention relates to preventing the reflux of fluids into an organ or the pleural cavity of a patient when fluid directing means or catheter means are utilized for removal of such fluids, which method comprises providing the catheter means or fluid directing means with the fluid flow control means described above; introducing the catheter or fluid directing means into the organ or pleural cavity of the patient; and removing fluids from the organ or pleural cavity by directing the fluid under a positive pressure into the bore of the input means of the fluid flow control means to facilitate the removal of such fluids by flow therethrough while preventing reflux of such fluids back into the patient.

BRIEF DESCRIPTION OF THE DRAWINGS

The nature, advantages, and various other additional features of the invention will appear more fully upon consideration of the illustrative embodiments now to be described in detail in connection with the accompanying drawing figures, wherein:

FIG. 2 is a front cross-sectional view of the valve of FIG. 1 to illustrate the positioning of the tubular member within the housing;

FIG. 3 is a side cross-sectional view of the valve of FIG. 1;

FIG. 4 is a perspective view of the valve of FIG. 1 with the exterior housing removed.

DETAILED DESCRIPTION OF THE PREFERRED EMBODIMENTS

Figure 1:
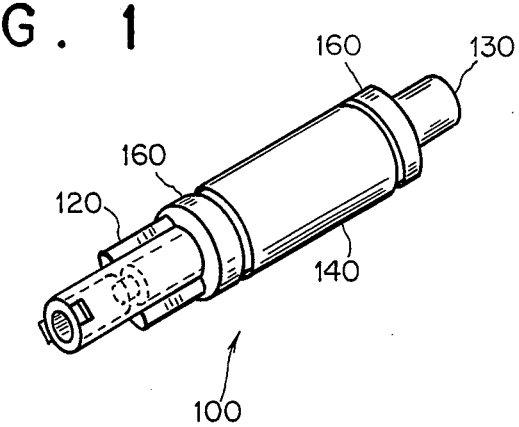
FIG. 1 is a perspective view of a valve structure according to the present invention.

In U.S. Pat. No. 4,684,364 there is disclosed a flow control device having a tubular structure with input means and output means each provided with an open bore, channel means connecting the input and output bores and operating between open and closed positions, and clip means for retaining a portion of the channel means in a prestressed condition to obturate the channels means so as to maintain it in a closed position. The channel means is forceable to an open position in response to a positive pressure in either one of the bores to facilitate flow through the channel means from the bore containing the positive pressure to the other bore. Also, the flow control device is capable of passing fluid in either direction depending upon which bore contains the positive pressure, with the clip means returning the channel means to the closed position when the positive fluid pressure is removed. This invention also includes an intravenous system comprising a source of intravenous fluid, first catheter means for insertion into the vascular system of a patient, a pump for performing a pumping operation and urging the fluid from the source to the first catheter means, second catheter means coupling the pump to the source, and the flow control device described above located in at least the first catheter means.

In U.S. Pat. No. 4,722,725, there is disclosed catheter means comprising an elongated body portion for insertion into a patient, at least one integral hub portion adjacent to the body portion, and at least one fluid flow control means located in either the body or hub portion or adjacent to the hub portion. The fluid flow control means may be integral with or releasably secured to its respective hub portion. Also, obturating means for rendering incompetent the fluid flow control means can be used.

The catheter means is intended for use in the methods disclosed in that patent. Such methods include preventing the introduction of ambient air into the vascular system of a patient when the catheter means is introduced into the patient's vascular system during intravenous or intra-arterial procedures, preventing the reflux of blood from the vascular system of the patient during such intravenous or intra-arterial procedures, and preventing the reflux of fluids into an organ or the pleural cavity of the patient when fluid directing means or catheter means are utilized for the removal of such fluids therefrom.

To the extent that the disclosure of the specification or drawings of either of these patents is necessary for an understanding of the present invention, the disclosures of the patents are expressly incorporated herein by reference thereto.

In the present invention, FIGS. 1–4 generally illustrate a fluid flow control means in the form of a valve arrangement 100. This valve includes exterior housing 110 and inlet and outlet connectors 120 and 130, shown having leur lock connections for releasable attachment to a catheter, tubing, or the like. Therefore, the valve can be connected to the catheters or intravenous systems described in either patent referred to above. A male extension 122, 132 which extends towards the center of the valve 100, is provided on the inlet and outlet connectors, 120, 130, respectively. A flexible tubular member 102 formed of a silicon tube or the like provides a channel between the input and output connectors 120, 130. The ends of tubular member 102 fit over the respective male ends 122 and 132 of connectors 120 and 130. The center portion of this tube 102 includes an internal disk member 104 which prestresses the tube and maintains it in a flattened condition in the area of the disk member. FIG. 3 best illustrates the flattened condition of the tube.

Figure 5:
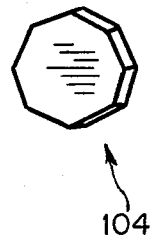
FIGS. 5 and 6 are views of disk prestressing means in octagonal and circular configurations, respectively.
Figure 6:
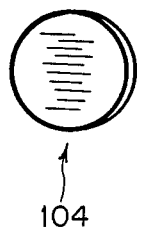

FIGS. 5 and 6 show a detail of various disks 104 in an octagonal and circular configuration, respectively. By making the width or diameter of these disks wider than the opening of the input or output connectors, the disk is prevented from leaving the central area of the tube where it is placed during manufacture of the valve. Also, the tube is maintained in an extended position by the placement of the input and output connectors in housing 140. This also prevents kinking or binding of the tube 104.

As shown in FIGS. 2 and 3, the housing 140 includes stop means 150, 152, in the form of an inwardly extending pin or plate, which maintains the distance between the input and output connectors at a predetermined distance when the valve is assembled. Of course, the input and output connectors have a corresponding hole or groove which matches the pin or plate of the housing 140.

Also to facilitate manufacture of the valve, the housing is split into two portions as best shown in FIG. 1. In the actual assembly of the valve, the disk 104 is initially placed inside the silicone tube 102 and the ends of the tube are then fitted around the male portion of the input and output connectors 120, 130. Next, top and bottom sides of housing 140 are placed around the input and output connectors and tube in a manner such that the stop means 150, 152 align properly with the groove means of the connectors. The two halves of the housing 140 can be held together by retaining rings 160 which slide over the end connectors and onto the terminal ends of the housing. If desired, the housing can be friction welded, ultrasonically welded, or glued with a suitable adhesive to create a permanent housing.

As mentioned above, the end connectors of this valve can be attached to catheters, tubing (shown in FIG. 4 as 170), intravenous systems, or the like. Such attachment techniques and preferred arrangements are illustrated in the drawings and descriptions of the preferred embodiments of the previous patents described above.

While it is apparent that the invention herein disclosed is well calculated to fulfill the objects above stated, it will be appreciated that numerous embodiments and modifications may be devised by those skilled in the art, and it is intended that the appended claims cover all such modifications and embodiments as fall within the true spirit and scope of the present invention.

We claim:

1. Fluid flow control means comprising:
   tubular means having open input and output bores connected by channel means and operable between an open position to allow fluid flow therethrough and a closed position to prevent ambient pressure air from passing therethrough;
   obturating means located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed;
   inlet and outlet connectors for insertion into said input and output bores, respectively of the tubular means for releasable attachment of the control means to fluid directing means; and
   housing means enclosing said tubular means and obturating means, and maintaining said inlet and outlet connectors at a predetermined spaced distance.

2. Fluid flow control means comprising:
   tubular means having open input and output bores connected by channel means and operable between an open position to allow fluid flow therethrough and a closed position to prevent ambient pressure air from passing therethrough; and
   obturating means comprising disc means for maintaining said tubular means in a substantially flat configuration located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position hen said positive pressure is removed.

3. The flow control means of claim 2 wherein the tubular means is a silicon tube.

4. The flow control means of claim 1 wherein said inlet and output connectors each include leur lock means to facilitate said releasable attachment.

5. The flow control means of claim 1 wherein the obturating means comprises disc means for maintaining said tubular means in a substantially flat configuration, and wherein the tubular means is a silicon tube.

6. Fluid flow control means comprising:
   tubular means having open input and output bores connected by channel means and operable between an open position to allow fluid flow therethrough and a closed position to prevent ambient pressure air from passing therethrough;
   obturating means comprising disc means located within said channel means for prestressing and maintaining a portion of said channel means in said closed position, said channel means beings forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed; and
   concentric housing means for enclosing said tubular means and obturating means.

7. The flow control means of claim 6 wherein said tubular means input and output bores are each connected to leur lock means to facilitate releasable attachment to fluid directing means, and wherein the tubular means is a silicon tube.

8. Catheter means comprising an elongated body portion for insertion into a patient; an integral hub portion adjacent to the body portion for introducing or removing fluids through the body portion; and fluid flow control means comprising:
   a tubular structure having input and output bores connected by channel means and operable between an open position to allow fluid flow therethrough and a closed position to prevent ambient pressure air from passing therethrough; and
   obturating means located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed.

9. The catheter means of claim 8 wherein the fluid flow control means is integral with said body portion.

10. The catheter means of claim 8 wherein the fluid flow control means is integral with said hub portion.

11. The catheter means of claim 8 which further comprises means to maintain the fluid flow control means in an open position to facilitate the introduction of second catheter means, trocar means, needle means or fluid directing means.

12. The catheter means of claim 11 wherein a first hub portion allows the introduction of a fluid into the body of the catheter means and a second hub portion allows a fluid to be removed from the body of the catheter means; the first hub portion including fluid flow control means which remains competent in response to fluid reflux or ambient air pressure but which opens in response to a positive fluid pressure above that of ambient air; the second hub portion including fluid flow control means which remains competent in response to fluid reflux but which opens in response to fluid pressure in the catheter body.

13. The catheter means of claim 8 wherein the fluid flow control means is releasably secured to the hub portion.

14. The catheter means of claim 8 wherein two integral hub portions are provided and each hub includes fluid flow control means located adjacent thereto.

15. The catheter means of claim 14 wherein the end of the body portion opposite the hub portion includes a plurality of apertures to facilitate fluid collection or removal.

16. The catheter of claim 8 wherein the obturating means comprises disc means for maintaining said tubular means in a substantially flat configuration and wherein the tubular means is a silicon tube.

17. The catheter of claim 8 wherein the flow control means further comprises concentric housing means for enclosing said tubular means and obturating means.

18. A method for preventing the introduction of air on reflux of blood flow into the vascular system of a patient through catheter means during intravenous or intra-arterial procedures which comprises:
   providing catheter means with fluid flow control means comprising:
   tubular means having open input and output bores connected by channel means and operable between an open position to allow fluid flow therethrough and a closed position to prevent ambient pressure air from passing therethrough; and
   obturating means located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed;
   introducing the catheter means into the vascular system of the patient during intravenous or intra-arterial procedures; and
   introducing a fluid into said patient through said fluid flow control means and catheter means by directing the fluid under a positive pressure into the bore of the input means of said fluid flow control means so that the fluid flow control means opens in response to said positive fluid pressure to allow flow therethrough, but remains competent in response to ambient air pressure in the bore of said input means to prevent the introduction of air into the vascular system of the patient.

19. A method for preventing the introduction of air or reflux or blood into the vascular system of a patient through catheter means during intravenous or intra-arterial procedures which comprises:

providing catheter means having fluid flow control means comprising:

tubular means having open input and output bores connected by channel means and operable between an open position to allow fluid flow therethrough and a closed position to prevent ambient pressure air from passing therethrough;

obturating means located within said channel means for prestressing and maintaining a portion of said channel means in said closed position, said channel means beings forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed; and concentric housing means for enclosing said tubular means and obturating means;

introducing the catheter means into the vascular system of the patient during intravenous or intra-arterial procedures; and introducing a fluid into said patient through said fluid flow control means and catheter means by directing the fluid under a positive pressure into the bore of the input means of said fluid flow control means so that the fluid flow control means opens in response to said positive fluid pressure to allow flow therethrough, but remains competent in response to ambient air pressure in the bore of said input means to prevent the introduction of air into the vascular system of the patient.

20. A method for preventing the introduction of air or reflux or blood into the vascular system of a patient through catheter means during intravenous or intra-arterial procedures which comprises:

providing catheter means comprising:

an elongated body portion for insertion into the patient; a hub portion adjacent to the body portion for introducing or removing fluids through the body portion; and fluid flow control means comprising:

a tubular structure having input and output bores connected by channel means and operable between an open position to allow fluid flow therethrough and a closed position to prevent ambient pressure air from passing therethrough; and obturating means located within said channel means for prestressing and maintaining a portion of said channel means in said closed position, said channel means being forceable to said open position in response to a positive fluid pressure in said input or output bore of said tubular means to allow fluid flow through said channel means form the bore containing the positive pressure to the other bore, said fluid flow control means capable of passing fluid in either direction depending upon which bore contains the positive pressure; said obturating means returning said channel means to said closed position when said positive pressure is removed;

introducing the catheter means into the vascular system of the patient during intravenous or intra-arterial procedures; and introducing as fluid into said patient through said fluid flow control means and catheter means by directing the fluid under a positive pressure into the bore of the input means of said fluid flow control means so that the fluid flow controls means opens in response to said positive fluid pressure to allow flow therethrough, but remains competent in response to ambient air pressure in the bore of said input means to prevent the introduction of air into the vascular system of the patient.

21. A method for preventing the reflux of fluids into an organ or the pleural cavity of a patient when fluid directing means is utilized for removal of such fluids, which comprises:

providing fluid directing means having fluid flow control means comprising:

tubular means having open input and output bores connected by channel means and operable between an open position to allow fluid flow therethrough and a closed position to prevent ambient pressure air from passing therethrough;

obturating means located within said channel means for prestressing and maintaining a portion of said channel means in said closed position, said channel means being forceable to said open position in response to a positive fluid pressure in said input or output bore of said tubular means to allow fluid flow through said channel means form the bore containing the positive pressure to the other bore, said fluid flow control means capable of passing fluid in either direction depending upon which bore contains the positive pressure; said obturating means returning said channel means to said closed position when said positive pressure is removed; and inlet and outlet connectors for insertion into said input and output bores, respectively, of the tubular means for releasable attachment of the control to means said fluid directing means;

introducing the fluid directing means into the organ or pleural cavity of a patient; and removing fluids from said organ or plural cavity by directing said fluid under a positive pressure into the bore of the input means of said fluid flow control means to facilitate removal of said fluids by flow therethrough while preventing the reflux of fluid or the introduction of air into the organ or pleural cavity of the patient.

22. A method for preventing the reflux of fluids into an organ or the pleural cavity of a patient when fluid directing means is utilized for removal of such fluids, which comprises:

providing fluid directing having fluid flow control means comprising:

tubular means having open input and output bores connected by channel means and operable between an open position to allow fluid flow therethrough and a closed position to prevent ambient pressure air from passing therethrough; and obturating means comprising disc means for maintaining said tubular means in a substantially flat configuration located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed;

introducing the fluid directing means into the organ or pleural cavity of a patient; and removing fluids from said organ or pleural cavity by directing said fluid under a positive pressure into the bore of the input means of said fluid flow control means to facilitate removal of said fluids by flow therethrough while preventing the reflux of fluid or introduction of air into the organ or pleural cavity of the patient.

23. A method for preventing the reflux of fluids into an organ or the pleural cavity of a patient when catheter means is utilized for removal of such fluids, which comprises:

introducing into an organ or pleural cavity of a patient catheter means comprising:
an elongated body portion for insertion into the patient; a hub portion adjacent to the body portion for introducing or removing fluids through the body portion; and fluid flow control means comprising:
a tubular structure having input and output bores connected by channel means and operable between an open position to allow fluid flow therethrough and a closed position to prevent ambient pressure air from passing therethrough; and
obturating means comprising disc means for maintaining said tubular means in a substantially flat configuration located within said channel means for prestressing and maintaining a portion of said channel means in said closed position, said channel means being forceable to said open position in response to a positive fluid pressure in said input or output bore of said tubular means to allow fluid flow through said channel means form the bore containing the positive pressure to the other bore, said fluid flow control means capable of passing fluid in either direction depending upon which bore contains the positive pressure; said obturating means returning said channel mean to said closed position when said positive pressure is removed; and removing fluids from said organ or pleural cavity by directing said fluid under a positive pressure into the bore of the input means of said fluid flow control means to facilitate removal of said fluids by flow therethrough while preventing the reflux of fluid or introduction of air into the organ or pleural cavity of the patient.

24. A method for preventing the reflux of fluids into an organ or the pleural cavity of a patient when catheter means is utilized for removal of said fluids, which comprises:

introducing into an organ or pleural cavity of a patient catheter means comprising:
an elongated body portion for insertion into the patient; a hub portion adjacent the body portion for introducing or removing fluids through the body portion; and fluid flow control means comprising:
a tubular structure having input and output bores connected by channel means and operable between an open position to allow fluid flow therethrough and a closed position to prevent ambient pressure air from passing therethrough; and
obturating means comprising disc means for maintaining said tubular means in a substantially flat configuration located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed; and removing fluids form said organ or pleural cavity by directing said fluid under a positive pressure into the bore of the input means of said fluid flow control means to facilitate removal of said fluids by flow therethrough while preventing the reflux of fluid or introduction of air into the organ or pleural cavity of the patient.

25. A method for preventing the reflux of fluids into an organ or the pleural cavity of a patient when catheter means are utilized for removal of such fluids, which comprises:

introducing into an organ or pleural cavity of a patient catheter means comprising:
an elongated body portion for insertion into the patient; at least two hub portions adjacent the body portion for introducing or removing fluids through the body portion; and fluid flow control means associated with each hub portion comprising:
tubular means having open input and output bores connected by channel means and operable between an open position to allow fluid flow therethrough and a closed position to prevent ambient pressure air from passing therethrough; and
obturating means located within said channel means for prestressing and maintaining a portion of said channel means in said closed position, said channel means being forceable to said open position in response to a positive fluid pressure in said input or output bore of said tubular means to allow fluid flow through said channel means from the bore containing the positive pressure to the other bore, said fluid flow control means capable of passing fluid in either direction depending upon which bore contains the positive pressure; said obturating means returning said channel means to said closed position when said positive pressure is removed; and removing fluids from said organ or pleural cavity by directing said fluid under a positive pressure into the bore of the input means of at least one of said fluid flow control means to facilitate removal of said fluids by flow therethrough while preventing the reflux of fluid or introduction into the organ or pleural cavity of the patient.

* * * * *